United States Patent
Jadhav et al.

(10) Patent No.: US 7,074,355 B2
(45) Date of Patent: *Jul. 11, 2006

(54) PROCESS FOR DRY GRANULATION BY AGITATIVE BALLING FOR THE PREPARATION OF CHEMICALLY STABLE, DRY-FLOW, LOW COMPACT, DUST FREE, SOLUBLE SPHERICAL GRANULES OF PHOSPHOROAMIDOTHIOATE

(75) Inventors: Prakash M. Jadhav, Mumbai (IN); Jai Shroff, Mumbai (IN)

(73) Assignee: United Phosphorus Ltd., Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 10/652,567

(22) Filed: Sep. 2, 2003

(65) Prior Publication Data

US 2005/0048094 A1 Mar. 3, 2005

(51) Int. Cl.
*B29B 9/08* (2006.01)
*A01N 25/12* (2006.01)

(52) U.S. Cl. .................. 264/115; 264/117; 514/120
(58) Field of Classification Search ............... 264/115, 264/117; 23/313 R; 514/120
See application file for complete search history.

(56) References Cited

U.S. PATENT DOCUMENTS

| | | | |
|---|---|---|---|
| 5,075,058 A | | 12/1991 | Chan |
| 5,100,667 A | * | 3/1992 | Chan et al. .................. 424/405 |
| 5,369,100 A | * | 11/1994 | Cummings .................. 514/120 |
| 5,464,623 A | * | 11/1995 | Chan et al. .................. 424/405 |
| 5,580,170 A | | 12/1996 | Holley |
| 6,013,272 A | * | 1/2000 | Cummings et al. ......... 424/408 |

* cited by examiner

*Primary Examiner*—Mary Lynn Theisen
(74) *Attorney, Agent, or Firm*—Jones, Tullar, Cooper, P.C.

(57) ABSTRACT

Chemically stable, dry-flow, low compact, dust free, soluble granules of phosphoroamidothioate are prepared using a substantially dry granulation process including an agitative balling process. In a preferred embodiment, spherically shaped acephate granules are produces without the intentional addition of water and/or solvents.

25 Claims, 2 Drawing Sheets

Figure 1:
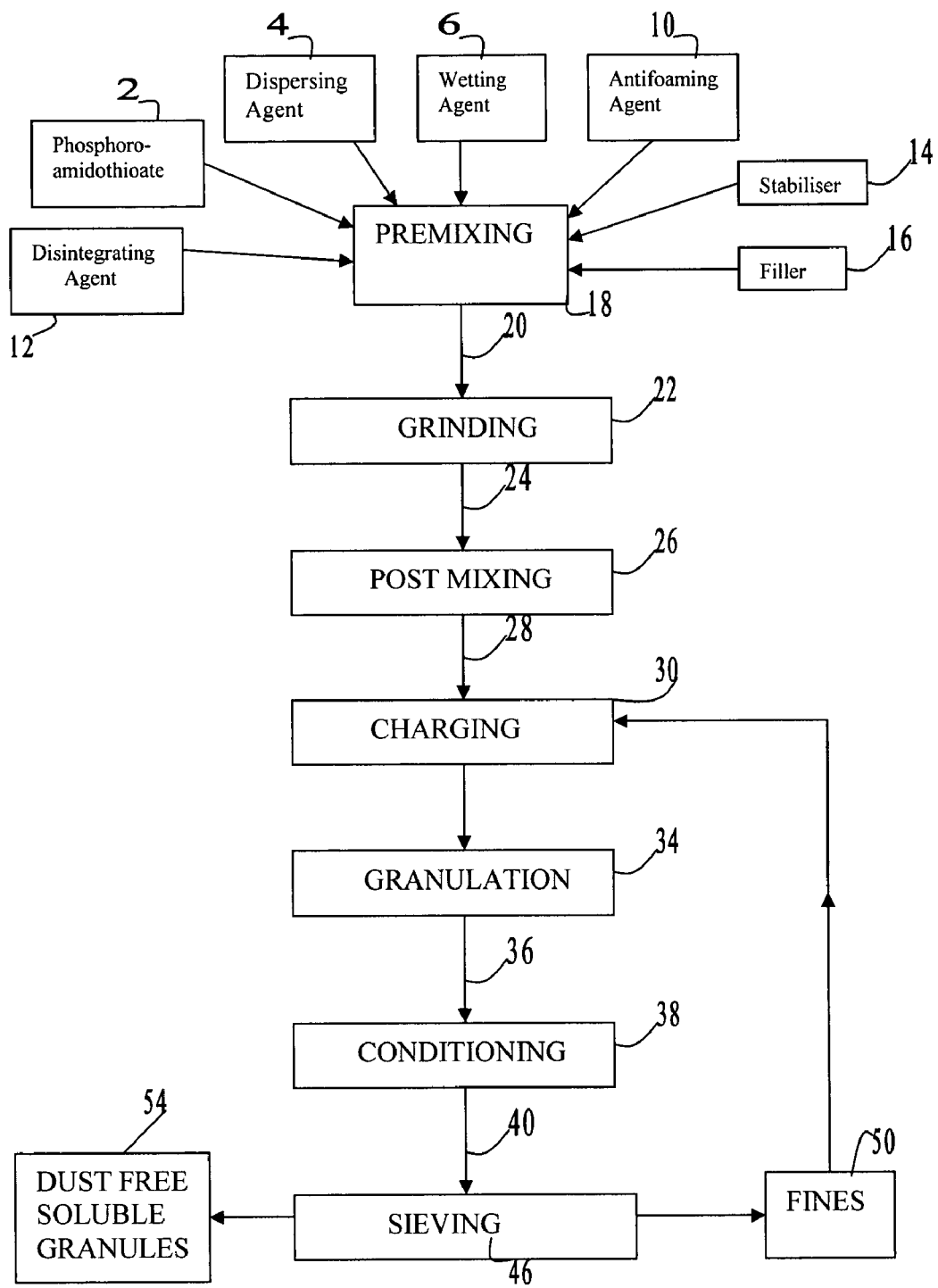

PROCESS FOR DRY GRANULATION BY AGITATIVE BALLING FOR THE PREPARATION OF CHEMICALLY STABLE, DRY-FLOW, LOW COMPACT, DUST FREE, SOLUBLE SPHERICAL GRANULES OF PHOSPHOROAMIDOTHIOATE

BACKGROUND OF THE INVENTION

1. Field of the Invention

The present invention relates to the preparation of chemically stable, dry-flow, low compact, dust free, soluble granules of phosphoroamidothioate using a substantially dry granulation process including an agitative balling process. This dry granulation process preferably produces spherical granules of phosphoroamidothioate without using substantial amounts of water, liquid, solvent or binder.

2. Description of Related Art

In recent years, agricultural chemicals have been most preferably formulated in the form of dusts, wettable powders, soluble powders, emulsifiable concentrates, soluble liquid/concentrates, granules, coated granules, water dispersible granules, suspension concentrates, and solutions. Occasionally, when dusts are produced by absorbing or mixing active ingredients with a finely divided inert carrier material, for example China Clay or the like, drift problems occur. With wettable powders and soluble powders the problems faced at the time of dilution are not only drift, but the final disposal of containers, for dust particles tend to stick to sides of the containers. The left over materials within the containers pose great problems to the environment, operators and users.

Although dusts are undesirable because of airborne contamination and handling difficulties, liquid spray formulations have not provided an acceptable alternative, for they involve solvents and packaging expenses, along with container disposal requirements that detract from their commercial desirability.

Water dispersible granules produced by fluidized bed spray dryers overcome the problems associated with wettable powders and soluble powders, but have high processing costs and require high value capital investment, as well as requiring highly skilled staff. These problems impose a significant barrier in widening the market acceptance of these compounds.

Certain phosphoroamidothioates and phosphoroamidodithioates, collectively referred to as phosphoroamidothioates, are known to have excellent insecticidal activity against a variety of insects and in a variety of environments. Acephate, one of the important commercial insecticides within this class of compounds, is a systemic and contact insecticide of moderate persistence with residual activity lasting about 10–15 days. It is effective against a wide range of aphids, leaf-miners, lepidopterous, larvae, sawflies and thrips and it is also a non-phytotoxic on many crop plants.

Phosphoroamidothioate containing pellets have been proposed in the past, but difficulties have been encountered in pelletizing acephate technical, the preferred insecticide within the class of phosphoroamidothioates. Attempts to manufacture acephate technical pellets from acephate technical powders have been proposed and have several disadvantages. As disclosed below, prior extrusion processes include the addition of costly surfactants, the combination of phosphoroamidothioate with a second active ingredient, or the creation of a mixture of the active ingredient with a solvent in an amount of from 3–25% by weight before extrusion.

One formulation of acephate presently in use is acephate 75% soluble powder having acephate active ingredient (a.i.) 75% (w/w), surfactant 1 to 2% (w/w), inert filler (precipitated silica) to make 100% (w/w). Acephate 75% soluble powder poses several problems including the production of dust, low pourability of the powder, high transportation costs, high capital manufacturing investment, measurement difficulties, difficulties in packing, material disposal, handling problems, high risk of caking and others.

A previous process for preparing pellets comprising insecticidal N-hydrocarboyl phosphoroamidothioates and/or phosphoroamidodithioates includes the extrusion of a solid composition. The concentration of the active ingredient in the pellets prepared is in the range of about 2 to 80% a.i., with the most likely concentration of 70% a.i. The process comprises (i) forming an extrudable mixture comprising the active ingredient; (ii) forming said pellets by extrusion of the mixture and cutting the extrudate. Another similar method comprises (i) forming a suspension or solution containing said active ingredient and a dispersant, wetting agent and/or surfactant; (ii) evaporating the solvent from said solution or dispersion; (iii) dividing the remaining solids into particles; and (iv) forming the resultant mixture into pellets. These processes experience several limitations and difficulties. First, the amount of active ingredient is in the range of about 2 to 80%, preferable being 70% so the process does not produce pellets having a concentration of active ingredient above 80%. Second, the process envisions two active ingredients namely N-hydrocarboyl phosphoroamidothioates and phosphoroamidodithioates in a single product. The selection of the combination of ingredients is important so that the product does not deteriorate in a few days to a few months. Third, the process involves forming a suspension or solution of the active ingredient and a dispersant, wetting agent and/or surfactant, and evaporating the solvent which are complicated processes and make the manufacturing process cumbersome and uneconomical.

In another previously used process for pelletizing insecticidal N-hydrocarboyl phosphoroamidothioates and phosphoroamidodithioates, the insecticidal ingredient in the pellets formed is in the range of about 50 to 95% preferably about 90%. This process involved mixing technical grade insecticide in a dry form with one or a mixture of surfactants (10% by weight of total dry composition) preferably containing an inert diluents ammonium sulfate (<40% of total pellet composition preferably 2% or less); solid additive (up to about 40% anhydrous Magnesium sulphate) and small amounts of deodorants and antifoam agents. The dry ingredients are ground to powdered form. Currently available pelletized acephate, known commercially as ORTHENE, requires the use of an anticaking agent, such as fumed silica. This process also has various limitations and difficulties. The amount of insecticidal ingredient present in these pellets is in the range of about 50 to 95%, preferably about only 90%. The final product may also contain inert diluents ammonium sulfate (<40% of total pellet composition preferably 2% or less) by weight of the total pellet composition. The presence of this agent is not desirable in the final product as it adds to the cost and imparts hardness to the granule when the active ingredient in the granule is in low concentration. The product may also include up to about 40% anhydrous magnesium sulphate, preferably 2% or less by weight of the total pellet composition, as a dehydrating agent to absorb trace amounts of the water present in the pellets to prevent hydrolysis of the insecticide. The presence of this agent is not desirable in the final product because it adds insoluble matter into the granules which causes problems in the application of the product.

In yet another previous process for forming pelletized insecticidal N-Hydrocarboyl phosphoroamidothioates and phosphoroamidodithioates, extrusion of a damp sandy loam of a dry mixture of the active ingredient and a solvent is formed. Several limitations and difficulties are associated with this process. First, the process involves mixing of active ingredient in a solvent to form a consistency of damp sandy loam and then pellets are formed by extrusion. Second, the process involves passing the mixture of active ingredient and the solvent in molten form through an orifice to form molten pellet-sized drops of said active ingredient and solidifying the said drops. These steps increase the processing costs of making the pellets because of the addition of costly solvents and the additional drying steps to remove the solvent and/or moisture.

One rapidly expanding field used in a variety of chemical processes is an agitative balling process for the formation of granules. Current processes used for making granules using the agitative balling process produce agglomerations and the resulting granules by admixing fine powder with binders, water or other types of liquids. The addition of binders, waters and other liquids increases the processing costs in formulating the granules.

Because of the problems associated with producing granular forms of phosphoroamidothioates, such as the preferred acephate, there is a need in the art for a process for preparing chemically stable, dry flow, low compact, dust free, insecticidally active soluble granules of phosphoroamidothioate which are useful from a practical stand point, as well as for a low cost, practical manufacturing technique which can be practiced on a commercial scale without requiring expensive additives or solvents.

BRIEF SUMMARY OF THE INVENTION

The problems associated with previous method for making chemically stable, dry flow, low compact, dust free, insecticidally active soluble granules of phosphoroamidothioate may be overcome by a substantially dry granulation process which uses an agitative balling process preferably producing spherical granules. Additional ingredients, such as specified adjuvants and other inert ingredients may be included in the dry granulation process and are preferably added as solids forming a dry pre-mix. The dry granulation process is performed without employing substantial amounts of water and/or solvent. In a preferred embodiment, no water and/or solvents are intentionally added at any stage of the process. The concentration of phosphoroamidothioate present in the resulting granules preferably varies from 75–99 wt. % phosphoroamidothioate. Acephate is the preferred phosphoroamidothioate.

The dry pre-mix is ground in a microniser and then the dry pre-mix is granulated using the agitative balling process through a granulator. The granulator is preferably provided with an external jacket heater to attain and maintain a processing temperature of preferably 115–145° F. The product is further passed through an air chamber to condition the granules for good surface finish. The conditioned product is then sieved for removal of fines, which are later recycled, resulting in chemically stable, dry flow, low compact, dust free, soluble granules of phosphoroamidothioate, preferably acephate. No sizing operation is required, which helps to avoid exposure and handling of dust.

In a preferred embodiment, the dry granulation process produces a spherical granule of phosphoroamidothioate without the intentional addition of water or any solvent in any step of the process. Since the dry granulation process avoids the use of water and/or solvent, the process is a free flowing process. Additionally, the dry granulation process avoids compacting or extruding of the material used to make the granules. By avoiding compaction and/or extrusion, the resulting granules have low compact and are readily soluble in water. Water soluble and insoluble powder can be mixed together in the absence of water to produce uniformly blended water dispersible granules.

The dry granulation process includes an agitative balling process, which utilizes a heat and balling conditioning of powder material. The present dry granulation process is a blend of technology relating to particle size enlargement and balling. The agitative balling process produces an agglomeration using binding force to achieve the granular shape by combining a brute force of agitation and a softening point of the material. The dry granulation process recognizes the distinct difference between forming pellets from powder and producing granules by an agitative balling process. More specifically, the agitative balling process described herein consolidates particles to produce a granular shape using external heat. The present dry granulation process shows that binding of dust particles can be achieved on account of the "binding tendency" induced in the dust particle at the softening point due to gentle heating. In one embodiment of the present invention, the phosphoroamidothioate used for the dry granulation process may have a trace concentration of process solvents, up to 1.0 wt. % max, preferably 0.5% max., which adds in attaining the softening of the material at lower temperature and enhances the compacting tendency to form granules.

BRIEF DESCRIPTION OF THE DRAWING(S)

Figure 2:
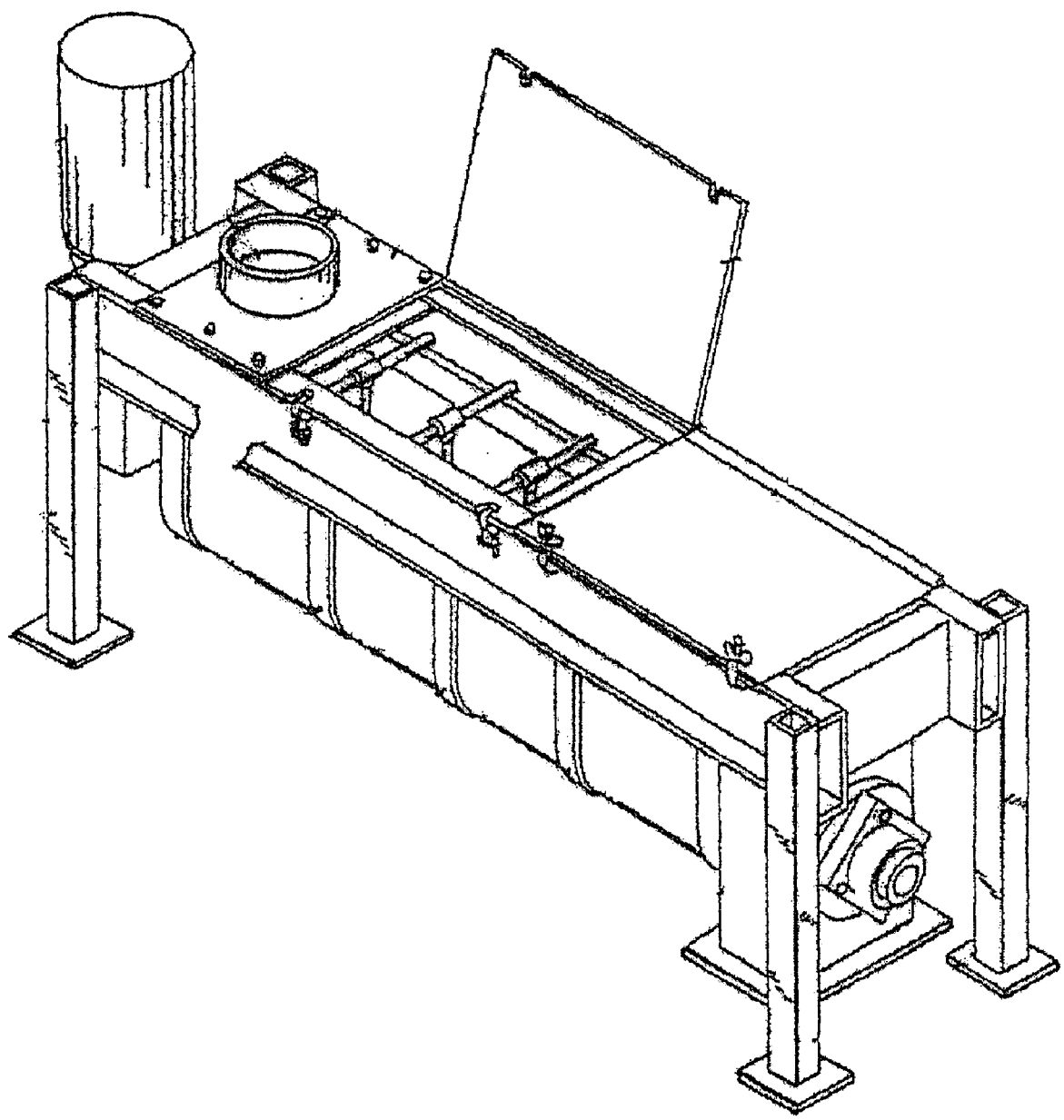

The features and advantages of the present invention will become apparent from the following detailed description of a preferred embodiment thereof, taken in conjunction with the accompanying drawing, in which:

FIG. 1 is a flow chart of a preferred embodiment of the present invention and FIG. 2 shows a preferred granulator used for the agitative balling process.

DETAILED DESCRIPTION OF THE INVENTION

The process of the present invention is best described by referring to the flow chart in FIG. 1. An essentially dry pre-mix is formed from the following ingredients: 75–99 wt. % phosphoroamidothioate 2, 0.1–5.0 wt. % dispersing agent (optional) 4, 0.1–3.0 wt. % wetting agent 6, 0.01–0.08 wt. % antifoaming agent (optional) 10, 0.01–10.0 wt. % disintegrating agent (optional) 12, 0.01–1.00 wt. % stabilizer (optional) 14, and fillers 16 to make 100 wt %. The preferred phosphoroamidothioate has the following formula:

Formula I

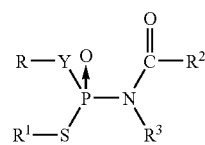

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur. All of the ingredients are preferably solids and in a powder form. In a preferred embodiment, the preferred dry pre-mix contains 75.0–99 wt. % phosphoroamidothioate 2, 0.1–3.0 wt. % wetting agent 6 and a filler 16 to make 100 wt. %. The preferred phosphoroamidothioate is acephate. In a preferred embodiment of the present invention the wetting agent 6 is a calcium or sodium salt of alkyl aryl sulphonate; the dispersing agent 4 is a derivative of sulfonated fatty alcohol; the disintegrating agent 12 is selected from swelling type clays like bentonite, zeolite ; the antifoaming agent 10 may be a silicon oil derivative; the stabilizer 14 is selected from salts of higher fatty acids; and the filler 16 is selected from precipitated silica, kaoline, bentonite, dolomite and the like. In a preferred embodiment, no water and/or solvents are intentionally added during the dry granulation process. However, if the processing temperature is low, a small amount of processing solvent, preferably 1.0 wt. %, may be added to enhance compaction.

The essentially dry pre-mix is subjected to pre-mixing 18 by charging the essentially dry pre-mix into a premixer and mixing to get a homogeneous pre-mixture 20. Grinding 22 of the pre-mix 20 is then conducted, preferably in a microniser to get a ground product 24 with particle size of 5 microns to 10 microns. The ground product 24 is subjected to post-mixing 26 to form a mixture 28 which is then made into granules 36 by preferably charging 30, by way of a rotary feeder, a feeding hopper which supplies the mixture 28 to a granulator for granulation 34.

FIG. 2 shows a preferred granulator which is generally disclosed in U.S. Pat. No. 5,580,170, hereby incorporated by reference. The granulator is a mixing and conditioning machine for turning dust and very fine particles into pellets and comprises an elongated, generally horizontal trough formed of flexible rubber like material having a downwardly concave arcuate bottom wall and vertical side walls. The granulator includes a rotor assembly comprising an elongated, generally horizontal shaft extending lengthwise within a trough with paddles distributed along the length of the shaft. The shaft is rotated to cause the paddles to mix and pelletize material introduced into the trough at an inlet end and move the material to an outlet end for discharge. The side walls of the trough are attached to the machine frame at points located a substantial distance above the bottom wall so that the trough is suspended from the points of attachment and enabled to flex as the shaft rotates, preventing build-up of material in the trough. Some of the paddles may have angled surfaced which urge the material towards the inlet end to increase the length of time the material remains in the trough and accordingly increase the amount of mixing of the material before it is discharged. The horizontal trough includes a thick abrasion resistant flexible liner, preferably a polyurethane liner, on its interior surface, which facilitates the maintenance of a critically closed tolerance required between the tips of the paddles and the flexible liner. Small particles making up the total particulate material are suspended with brute force within the housing through the physical and aerodynamic forces present while the very intensive mixing action occurs in the turbulent wake or vortex created behind the paddles. The densifying action essentially eliminates the oxygen or air trapped between the paddles for a continuous discharge into the feed outlet. The granules that are formed travel from one end of the trough to the other end of the trough and finally to the bottom part of the trough upon attaining a tumbling load. The fine particles remain closer to the top of the trough and are retained within the concave trough for further growth. The arrangement of the blades of the paddles is varied to accomplish the specific purpose according to properties of powder to be granulated. The size of granules being produced can be controlled by the speed of the rotor, the temperature of material and the length of mixing time. The granulator is preferably provided with an external jacket heater to attain and maintain a preferred processing temperature of 115 to 140° F. for turning dust and very fine particles into granules. If the temperature of the agitation is raised to a range of 120 to 140° F., granulation can occur without the intentional addition of any type of solvents, water or binders. The uniformity of the granule size is greatly influenced by the arrangement of the blades of the paddles. The operation of agitative balling is restricted by the need to satisfy the following critical parameters: 1) the speed of agitation; 2) the depth of the material in residence of the concave 3) the temperature of the material; 4) the time required for agitative balling; 5) the clearance between the paddles and the trough wall; and 6) the type of flexible liner. Illustrations of these critical parameters are disclosed in the preferred Examples provided below.

The resulting granules 36 are subjected to a conditioning process 38, preferably by passing the granules 36 through an air chamber, producing conditioned granules 40. The conditioned granules are then subjected to sieving 46 to separate fines 50 from desired dust free soluble granules 51.

The fines 50 from the sieving 46 process may be collected and recycled at the charging 30 stage of the process to obtain a minimum yield of 99.0% dry flowable, low compact, dust free, soluble granules 54 of phosphoroamidothioates, preferably acephate.

The granules of phosphoroamidothioate prepared by the process of the invention are useful as they have odor control, good pourability, high a.i., low capital investment, easy to handle, limited risk of caking, good dispersibility, easily reproducible during processing, very high degree of flowability, easy to measure, and a uniform size. Since the granules undergo agitative balling in repetitive manner till acquiring size and load, before they leave the trough a layering type of granulation are attained forming well rounded granules of excellent dispersibility.

The following examples are presented to illustrate but not to restrict the present invention. Parts and percentage are by weight unless otherwise specified.

EXAMPLE-1

Acephate 97% Granules can be prepared as follows:

| Composition | |
|---|---|
| Ingredients | Quantity (% w/w) |
| Acephate technical 98.5% purity | 98.48 |
| Dispersing agents (Dispersol-PS) | 0.50 |
| Wetting agent (Lisapol-D) | 0.10 |
| Antifoaming agent (Agnique Soap-L) | 0.03 |
| Disintegrating agents (Bentonite) | 0.50 |

-continued

| Composition | |
|---|---|
| Ingredients | Quantity (% w/w) |
| Stabilizers (Salts of higher fatty acids) | 0.05 |
| Filler(s) (Kaoline) | 0.34 |
| TOTAL | 100.00% w/w |

The constituents of the above composition are mixed in a pre-mixer, then micronised and ground in a microniser to the required size of 5 to 50 microns homogeneous mixture. This mixture is then fed through a feeder into a granulator and agglomerated for 1 to 1.5 hour using the agitative balling process. The granulator has a cylindrical trough having an interior lining made of rubber/PV sheet, where the material fills $\frac{1}{3}^{rd}$ of the trough. The clearance between the paddles and the trough wall is 1.5–2.0 mm. The trough has an external jacket heater to attain and maintain a processing temperature of 115–125° F. The paddles are rotated at 250–300 RPMs. The acephate granules are further conditioned using an air chamber and are collected after sieving. The fines generated during the process are recharged to get the conversion yield of 99 percent.

EXAMPLE-2

Acephate 90% Granules can be prepared as follows:

| Composition | |
|---|---|
| Ingredient | Quantity (% w/w) |
| Acephate technical 98.5% purity | 91.38 |
| Dispersing agents (Dispersol-PS) | 1.75 |
| Wetting agent (Lisapol-D) | 1.50 |
| Antifoaming agent (Agnique Soap-L) | 0.03 |
| Disintegrating agents (Bentonite) | 1.00 |
| Stabilizers (Salts of higher fatty acids) | 0.50 |
| Fillers (Kaoline) | 3.84 |
| TOTAL | 100.00% w/w |

Acephate 90% granules with above composition can be prepared by following the process described in EXAMPLE-1.

EXAMPLE-3

Acephate 85% granules can be prepared as follows:

| Composition | |
|---|---|
| Ingredient | Quantity (% w/w) |
| Acephate technical 98.5% purity | 86.30 |
| Dispersing agents (Dispersol-PS) | 2.25 |
| Wetting agent (Lisapol-D) | 2.00 |
| Antifoaming agent (Agnique Soap-L) | 0.05 |
| Disintegrating agents (Bentonite) | 2.00 |
| Stabilizers (Salts of higher fatty acids) | 0.60 |
| Fillers (Kaoline) | 6.80 |
| TOTAL | 100.00% w/w |

Acephate 85% granules with above composition can be prepared by following the process described in EXAMPLE-1 with the proviso that the process temperature is 145° F., the RPM is 350–400, the clearance between the paddles and the trough wall is 1.25–1.75 mm, and the processing time is 2.5–3 hours.

EXAMPLE-4

Acephate 75% Granules can be prepared as follows:

| Composition | |
|---|---|
| Ingredient | Quantity (% w/w) |
| Acephate technical 98.5% purity | 76.15 |
| Dispersing agents (Dispersol-PS) | 3.50 |
| Wetting agent (Lisapol-D) | 3.50 |
| Antifoaming agent (Agnique Soap-L) | 0.06 |
| Disintegrating agents (Zeolex) | 5.00 |
| Stabilizers (Salts of higher fatty acids) | 0.75 |
| Fillers (Kaoline) | 11.04 |
| TOTAL | 100.00% w/w |

Acephate 75% Granules with above composition can be prepared by following the process described in EXAMPLE-3.

TESTS

The physical properties of Acephate granules prepared by the dry granulation process of the present invention were determined before and after aging at 45° C. for 500 hrs. Tests performed included flowability, wetting time, attrition test, disintegration rate, tap density, suspensibility, sedimentation and persistent foam. The dynamic wetting time and solubility test were measured as per MT-167 of CIPAC. The flowability was measured as per MT-172 of CIPAC. The dry sieve analysis was measured as per MT-170 of CIPAC. The sedimentation was measured as per MT-15.1 of CIPAC. Dustiness of granules was measured as per MT-171 of CIPAC. The tap density was measured as per MT-58.4 and MT-33 of CIPAC. The Acephate technical content was determined by GLC method published in AOAC. No noticeable problems relating to the properties of the granules were observed in the above-listed tests.

Although the present invention has been disclosed in terms of a preferred embodiment, it will be understood that numerous additional modifications and variations could be made thereto without departing from the scope of the invention as defined by the following claims:

We claims:
1. A process for preparing soluble granules comprising,
 a) premixing 75 to 98 wt. % a phosphoroamidothioate compound of the following formula:

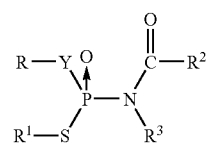

wherein R and $R^1$ individually are an alkyl, alkenyl or alkynyl group containing up to 6 carbon atoms, $R^2$ is hydrogen, an alkyl group containing 1 to 18 carbon atoms, a cycloalkyl group containing 3 to 8 carbon atoms, an alkenyl group containing 2 to 18 carbon atoms or an alkynyl group containing 3 to 18 carbon atoms, $R^3$ is hydrogen or an alkyl group containing 1 to 6 carbon atoms, and Y is oxygen or sulfur; 0.1–3.0 wt. % a wetting agent and a filler to make 100 wt. %, to form a substantially dry premix;
  b) grinding said substantially dry premix to produce a ground product having a predetermined particle size;
  c) post-mixing said ground product to produce a mixture;
  d) granulating said mixture using an agitative ball process to produce granules;
  e) conditioning said granules to produce conditioned granules; and
  f) sieving said conditioned granules to separate fines which are less than a predetermined granular size.

2. The process of claim 1, wherein said agitatative ball process includes heating said mixture at a processing temperature using external heating.

3. The process of claim 2, wherein said processing temperature is 120–140° F.

4. The process of claim 1, wherein said wetting agent is selected from the group comprising calcium salt of alkyl aryl sulphonate and sodium salt of alkyl aryl sulphonate.

5. The process of claim 1, wherein said filler is selected from the group comprising precipitated silica and kaoline.

6. The process of claim 5, wherein said wetting agent is selected from the group comprising calcium salt of alkyl aryl sulphonate and sodium salt of alkyl aryl sulphonate.

7. The process of claim 1, wherein said step of premixing to form said dry premix further comprises premixing 0.1–5.0 wt. % a dispersing agent.

8. The process of claim 7, wherein said dispersing agent is a derivative of sulfonated fatty alcohol.

9. The process of claim 1, wherein said step of premixing to form said dry premix further comprises premixing 0.01–0.08 wt. % an antifoaming agent.

10. The process of claim 9, wherein said antifoaming agent is a silicon oil derivative.

11. The process of claim 1, wherein said step of premixing to form said dry premix further comprises premixing 0.01–10 wt. % a disintegrating agent.

12. The process of claim 11, wherein said disintegrating agent is a swelling type clay selected from the group comprising bentonite and zeolite.

13. The process of claim 1, wherein said step of premixing to form said dry premix further comprises premixing 0.01–1.0 wt. % a stabilizer.

14. The process of claim 13, wherein said stabilizer is a salt of a higher fatty acid.

15. The process of claim 1, wherein said phosphoroamidothioate compound is acephate.

16. The process of claim 1, further comprising;
  g) recycling said fines into step d).

17. The process of claim 16, wherein said phosphoroamidothioate compound is acephate.

18. The process of claim 1, wherein said substantially dry premix is essentially free from water or solvent.

19. The process of claim 1, wherein said substantially dry premix includes up to 1 wt. % solvent.

20. The process of claim 1, wherein said step of premixing to form said dry premix further comprises premixing 0.1–5.0 wt. % a dispersing agent, 0.01–0.08 wt. % an antifoaming agent, 0.01–10 wt. % a disintegrating agent, 0.01–1.0 wt. % a stabilizer.

21. The process of claim 20, wherein said phosphoroamidothioate compound is acephate.

22. The process of claim 21, wherein said dispersing agent is a derivative of sulfonated fatty alcohol, said antifoaming agent is a silicon oil derivative, said disintegrating agent is selected from the group comprising bentonite and zeolite, and said stabilizer is a salt of a higher fatty acid.

23. The process of claim 22, wherein said substantially dry premix is substantially free of water or solvent.

24. The process of claim 20, wherein said substantially dry premix is substantially free of water or solvent.

25. The process of claim 1, wherein said granules are spherical granules.

* * * * *